(12) United States Patent
Groen et al.

(10) Patent No.: US 9,556,233 B2
(45) Date of Patent: Jan. 31, 2017

(54) CYCLOHEXAPEPTIDE

(71) Applicant: DSM SINOCHEM PHARMACEUTICALS NETHERLANDS B.V., Delft (NL)

(72) Inventors: Paulus Bernardus Maria Groen, Echt (NL); Peter Philip Lankhorst, Echt (NL); Burhan Özalp, Echt (NL); Robertus Mattheus De Pater, Echt (NL)

(73) Assignee: DSM SINOCHEM PHARMACEUTICALS NETHERLANDS B.V., Delft (NL)

( * ) Notice: Subject to any disclaimer, the term of this patent is extended or adjusted under 35 U.S.C. 154(b) by 0 days.

(21) Appl. No.: 14/915,997

(22) PCT Filed: Sep. 8, 2014

(86) PCT No.: PCT/EP2014/069050
§ 371 (c)(1),
(2) Date: Mar. 2, 2016

(87) PCT Pub. No.: WO2015/036354
PCT Pub. Date: Mar. 19, 2015

(65) Prior Publication Data
US 2016/0215021 A1 Jul. 28, 2016

(30) Foreign Application Priority Data
Sep. 11, 2013 (EP) ..................................... 13183974

(51) Int. Cl.
*C07K 7/56* (2006.01)

(52) U.S. Cl.
CPC ....................................... *C07K 7/56* (2013.01)

(58) Field of Classification Search
None
See application file for complete search history.

(56) References Cited

U.S. PATENT DOCUMENTS

2009/0291996 A1   11/2009   Korodi et al.
2009/0324635 A1   12/2009   Korodi et al.

OTHER PUBLICATIONS

International Search Report for PCT/EP2014/069050, mailed Dec. 11, 2014, 4 pages.
Written Opinion of the ISA for PCTEP2014/069050, mailed Dec. 11, 2014, 4 pages.
Leonard et al., "Synthesis of the Antifungal [beta]-1,3-glucan synthase inhibitor Cancidas (caspofungin acetate) from pneumocandin BO", The Journal of Organic Chemistry, vol. 72, No. 7, Mar. 30, 2007, pp. 2335-2343.

*Primary Examiner* — Thomas S Heard
(74) *Attorney, Agent, or Firm* — Nixon & Vanderhye P.C.

(57) ABSTRACT

The present invention relates to a novel cyclohexapeptide, to a method for the preparation of said cyclohexapeptide and to the use of said cyclohexapeptide.

12 Claims, 4 Drawing Sheets

CYCLOHEXAPEPTIDE

Figure 1:
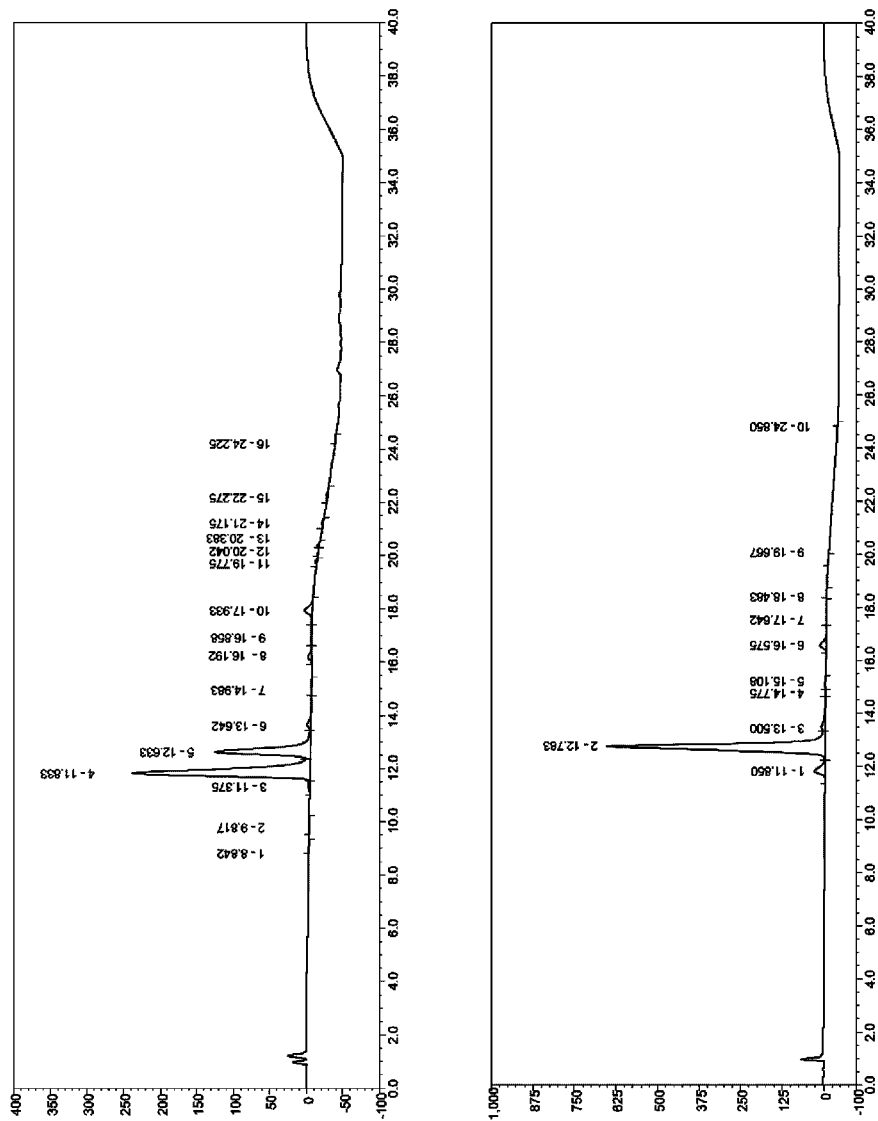

This application is the U.S. national phase of International Application No. PCT/EP2014/069050 filed 8 Sep. 2014, which designated the U.S. and claims priority to EP 13183974.8 filed 11 Sep. 2013, the entire contents of each of which are hereby incorporated by reference.

FIELD OF THE INVENTION

The present invention relates to a novel cyclohexapeptide, to a method for the preparation of said cyclohexapeptide and to the use of said cyclohexapeptide.

BACKGROUND OF THE INVENTION

Cyclopeptides are polypeptides in which the terminal amine and carboxyl groups form an internal peptide bond. Several cyclopeptides are known for their advantageous medicinal properties. An excellent example of this is the class of echinocandins which are potent antifungals. Echinocandins inhibit the synthesis of glucan in the cell wall through noncompetitive inhibition of the enzyme 1,3-β-glucan synthase. Echinocandins are used in candidiasis and aspergillosis, they are fungicidal against some yeasts (most species of *Candida*), fungistatic against some molds and modestly or minimally active against dimorphic fungi (*Blastomyces* and *Histoplasma*). Also they have activity against the spores of the fungus *Pneumocystis carinii*.

Echinocandins can be naturally occurring compounds but may also be obtained by total synthesis or by synthetic or genetic modification of naturally occurring or naturally produced precursors; the latter class is referred to as semi synthetic echinocandins. One of the first echinocandins of the pneumocandin type, echinocandin B, could not be used clinically due to risk of high degree of hemolysis. However, preparation and screening of semi synthetic analogs of the echinocandins resulted in to cilofungin, the first echinocandin analog to enter clinical trials. Later semi synthetic pneumocandin analogs of echinocandins were found to have similar or improved antifungal activity with lower toxicity. The first approved of these newer echinocandins was caspofungin, and later micafungin and anidulafungin were also approved. Anidulafungin, caspofungin and micafungin are all semi synthetic echinocandins derivable from naturally occurring echinocandins such as echinocandin B, pneumocandin $A_0$, or pneumocandin $B_0$. One drawback of the compounds currently available to the market is low oral bioavailability, and hence they must be administered intravenously. Nevertheless, echinocandins have now become one of the first line treatments for *Candida*, but also for treating fungal infections caused by *Aspergillus, Blastomyces, Coccidioides* and *Histoplasma*.

Although nature can provide a substantive part of the complex chemical structure of semi synthetic cyclopeptides, and in many cases having all chiral centers in the required configuration, a major disadvantage nevertheless is that during fermentation often side products are formed that carry through the process and eventually end up as impurities. Only in few cases can fermentation processes be tuned in such a way as to prevent formation of impurities. Particularly when these impurities are structurally closely related to the main product, their removal is usually tedious and often requires unprecedented purification approaches as the main products in question are chemically unstable and/or prone to racemization.

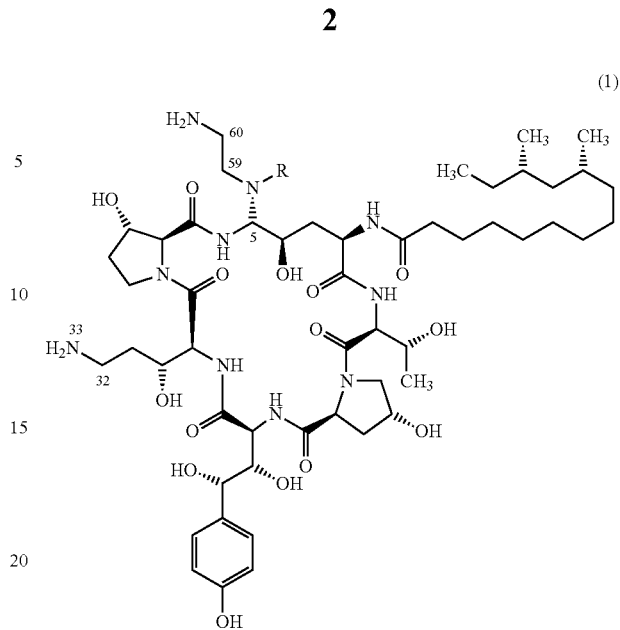

(1)

More specifically, the preparation of caspofungin ((1), R=H) from fermentatively obtained pneumocandin $B_0$ is a process wherein control of impurities is an important issue and indeed control of impurities has been the subject of several earlier studies such as, for example, US 2009/0291996 and US 2009/0324635 and references cited therein. Further improvement of impurity control in caspofungin production is one of the foundations of the invention as herein described. Upon preparation of caspofungin registration batches it was observed in certain HPLC traces that a shoulder is present on the descending side of the main caspofungin peak; this shoulder has hitherto not been described in literature. Although the cause of this phenomenon, i.e. the formation of an unwanted by-product, is at present unknown, the problem underlying the present invention is the determination of the chemical structure of the compound in question and the design of analytical methodology to establish presence or absence of this impurity in caspofungin batches.

In addition, another objective is to provide new pharmaceutically active compounds with the goal to further improve the spectrum of antifungal drugs available for treatment of fungal infections. The latter is of relevance in view of the problem of continuously developing resistance against existing drugs.

DETAILED DESCRIPTION OF THE INVENTION

It is an object of the present invention to improve analysis and purification of echinocandin active pharmaceutical ingredients. Specifically it is an object of the present invention to predict, identify and obtain unwanted compounds that may occur in caspofungin production and storage under certain conditions to which caspofungin may be exposed, such as humidity, high temperature or, as is the case in the present invention, oxidative circumstances. More specifically it is the object of the present invention to identify, obtain and apply in analytical procedures an impurity that has hitherto not been reported. In addition it is an object of the present invention to identify and isolate new compounds with possible antifungal properties.

In a first aspect, the invention provides a compound of general formula (1) wherein R is hydroxyl or a salt thereof. The term "caspofungin hydroxylamine" as used herein refers to said compound of general formula (1) wherein R is hydroxyl. Since caspofungin hydroxylamine likely is pharmaceutically active as an antifungal, the salts of caspofungin hydroxylamine are preferably pharmaceutically acceptable salts. The term "pharmaceutically acceptable salt" as used herein means non-toxic salts of caspofungin hydroxylamine, and includes mono- and di-acid forms which are usually prepared by reacting caspofungin hydroxylamine (i.e. the free base) with a suitable organic or inorganic acid. Pharmaceutically acceptable salts suitable as acid addition salts as well as salts providing the anion of the quaternary salt are those from acids such as hydrochloric, hydrobromic, phosphoric, sulfuric, lactic, maleic, acetic, citric, tartaric, propionic, succinic, oxalic, malic, glutamic, pamoic acid and the like, and include other acids related to the pharmaceutically acceptable salts listed in Berge S. M. et al. (*J. Pharm. Sci.* (1977) 66 (1), 1-19), and acids related to the counter ions in salt forms as listed in Strickley R. G. (*J. Pharm. Sci. Technol.* (1999) 53 (6), 324-349). Preferred examples of pharmaceutically acceptable salts are acid addition salts with an organic acid comprising at least one organic acid selected from the group consisting of acetic, citric, glutamic, lactic, maleic, malic, oxalic, pamoic, propionic, succinic and tartaric acid. A most preferred example is the diacetate of caspofungin hydroxylamine.

In one embodiment caspofungin hydroxylamine or a salt thereof is the major or only constituent of a composition. Such composition has various uses such as analytical and/or pharmaceutical as further specified in the third aspect of the present invention.

In another embodiment caspofungin hydroxylamine or a pharmaceutically acceptable salt thereof is part of a composition comprising said compound in combination with a compound of general formula (1) wherein R is hydrogen, i.e. caspofungin. Preferably said composition comprises caspofungin hydroxylamine in an amount of from 0.01% to 2% based on weight, more preferably in an amount of from 0.02% to 1.5% based on weight, most preferably in an amount of from 0.025% to 1.0% based on weight.

In another embodiment caspofungin hydroxylamine or a salt thereof or the composition comprising said compound is in amorphous form. Such form preferably is a lyophilized powder. Thus, the present invention further provides a pharmaceutical composition in a solid form, e.g. in the form of a powder, preferably in the form of a lyophilized powder which is obtainable, preferably obtained, by lyophilization of an aqueous solution, preferably of the solution obtained by a chromatographic procedure as described in the second aspect of the invention. Prior to lyophilization, the solution obtained following chromatography may optionally be followed by desalination techniques known to the skilled person. The lyophilized powder ultimately obtained is suitable for making a liquid for obtained by parenteral administration, such as injectable formulations for subcutaneous, intravenous, intra-peritoneal or intramuscular administration, preferably intravenous administration.

In a second aspect, the present invention provides a method for the preparation of caspofungin hydroxylamine comprising contacting caspofungin or a salt thereof with an oxidizing agent. In a preferred option said method is further expanded with purification and isolation. Purification can be achieved advantageously using chromatography. Chromatography may be carried out using normal or reversed phase techniques. In a preferred embodiment chromatography is carried out under reversed phase conditions, i.e. using a hydrophobic stationary phase. Preferably such hydrophobic stationary phase comprises alkyl chains covalently bonded to a solid support. Reversed phase chromatography employs a polar, preferably aqueous, mobile phase. Any inert non-polar substance that achieves sufficient packing can be used for reversed-phase chromatography. Preferably octadecyl carbon chain ($C_{18}$)-bonded silica (USP classification L1) is used as stationary phase but alternatives such as $C_8$-bonded silica (L7), pure silica (L3), cyano-bonded silica (L10) and phenyl-bonded silica (L11) are also suitable. The stationary phase can have different polarities such as available through various functionalities known to the skilled person. Suitable examples are pentafluorphenyl, cyano, octadecyl or mixed functionalities such as ODCN (mixed mode column consisting of $C_{18}$ and nitrile). The mobile phase may be a single phase but preferably comprises two phases that are applied in a gradient. A first phase may be an aqueous buffer and the second phase may be an aqueous organic solvent. Said organic solvent advantageously also is present in said first phase. Suitable first phase are aqueous buffers comprising ammonium, potassium or sodium salts. Such salts may be carbonates, citrates, phosphates and the like. The organic solvent that is part of the second phase and may also be part of the first phase may be acetone, acetonitrile, ethanol, methanol and the like. Preferably said solvent is acetonitrile. The pH of the aqueous buffer of said first phase preferably is from 5 to 9, more preferably from 6 to 8, most preferably from 6.5 to 7.5.

Oxidation may be effected by means of a wide variety of oxidizing agents known to the skilled person, amongst which air and oxygen. Preferably said oxidation is achieved with an oxidizing agent that is a peroxyacid. In a preferred embodiment said peroxyacid is chosen from the list consisting of m-chloroperoxybenzoic acid, peracetic acid, peroxymonosulphuric acid and peroxyphosphonic acid. Oxidation may be carried out with or without solvent. Preferably a solvent is used and preferably said solvent is sufficiently inert to oxidative conditions. Preferred solvents are organic acids and alcohols, examples of which are acetic acid, ethanol, formic acid, methanol, propanol, propionic acid and the like or mixtures thereof.

In one embodiment, caspofungin hydroxylamine may be isolated after purification, e.g. by chromatography. Isolation may be effected by various techniques available to the skilled person. A preferred method of isolation is lyophilization. Lyophilization may e.g. be performed as follows, e.g. by subjecting a container containing suitable amounts of an aqueous solution comprising caspofungin hydroxylamine or a salt thereof to lyophilization until a cake is formed at the bottom of the container by using a freeze drier, for example as commercially available as Christ Epsilon 2-6 D™ freeze-drier. In one embodiment, primary drying may be performed at a temperature of −40±10° C. and at a pressure of 0.05±0.04 mbar for about 16-24 h. Secondary drying may be performed at 15±10° C. within about 3 hours at a vacuum of about 0.01±0.005 mbar. Process parameters may be adapted for varying filling heights of the containers and process time for individual steps of lyophilization may be adjusted to ensure complete drying of compositions according to known methods. Lyophilization may optionally be preceded by desalination to remove excess salts.

In a third aspect, the present invention provides the use of caspofungin hydroxylamine.

In one embodiment said use may be the application as antifungal agent. Given the fact that the compound of the present invention is an echinocandin and this class is well known for its advantageous antifungal properties, antifungal activity is expected also for caspofungin hydroxylamine or a pharmaceutically acceptable salt thereof. This is emphasized by virtue of the very close resemblance to caspofungin, one of the most successful echinocandins. Since caspofungin hydroxylamine is of a higher oxidation state than caspofungin, it has the additional advantage that it is less prone to formation of oxidative impurities and consequently easier to store for longer periods of time. Thus the present invention provides the use of caspofungin hydroxylamine or a pharmaceutically acceptable salt thereof as a medicament for preventing and/or treating mycotic infections in mammals, in particularly those caused by *Candida* species and by *Aspergillus* species. Preferably the caspofungin hydroxylamine or a pharmaceutically acceptable salt thereof is the pharmaceutically active ingredient present in a therapeutically effective amount in a composition. If administered intravenously, the most preferred doses of active ingredient will range from about 1 $\mu g \cdot kg^{-1} \cdot min^{-1}$ to about 50 $\mu g \cdot kg^{-1} \cdot min^{-1}$ with an infusion rate of approximately 200 $ml \cdot h^{-1}$. For such administration, the composition of the invention should comprise from 0.025 $mg \cdot ml^{-1}$ $mg \cdot ml^{-1}$ of caspofungin hydroxylamine based on a mammal having a weight of 50 kg, as is described in EP 904098B1. The present invention further provides a pharmaceutical composition comprising caspofungin hydroxylamine diacetate in crystalline or amorphous form, and optionally additionally one or more pharmaceutically acceptable excipients known in the art.

In another embodiment said use may be the determination of the quality of a caspofungin sample. Since caspofungin samples may come in contact with oxidizing agents, the unwanted formation of traces of caspofungin hydroxylamine in said caspofungin samples is conceivable and should be limited as best as possible in order to comply with regulatory requirements. Accordingly, the present invention provides access to caspofungin hydroxylamine which may be used in analytical procedures such as a standard or reference for analytical purposes, such as qualitative or quantitative HPLC. In one embodiment such HPLC analysis preferably is reversed phase HPLC using HPLC systems known to the skilled person. Suitable examples are $C_{18}$ columns using two-eluent systems. Suitable eluents may be combinations of aqueous buffers and organic solvents. Particularly suitable is the combination of an aqueous phosphate buffer such as potassium or sodium phosphate and acetonitrile. A suitable pH range for performing the analytical use is from 6.0 to 8.0, preferably from 6.5 to 7.5.

LEGEND TO THE FIGURES

FIG. 1 is the HPLC chromatogram of a reaction mixture comprising caspofungin and peracetic acid (left panel when seen in portrait mode; the mixture of Example 1 at t=5 min) and of caspofungin hydroxylamine ((1) with R is hydroxyl) after purification (right panel when seen in portrait mode). X-axis: retention time in minutes; Y-axis: UV absorbance. The caspofungin peak is at 11.6±0.3 minutes, the peak of caspofungin hydroxylamine is at 12.7±0.2 minutes.

Figure 2:
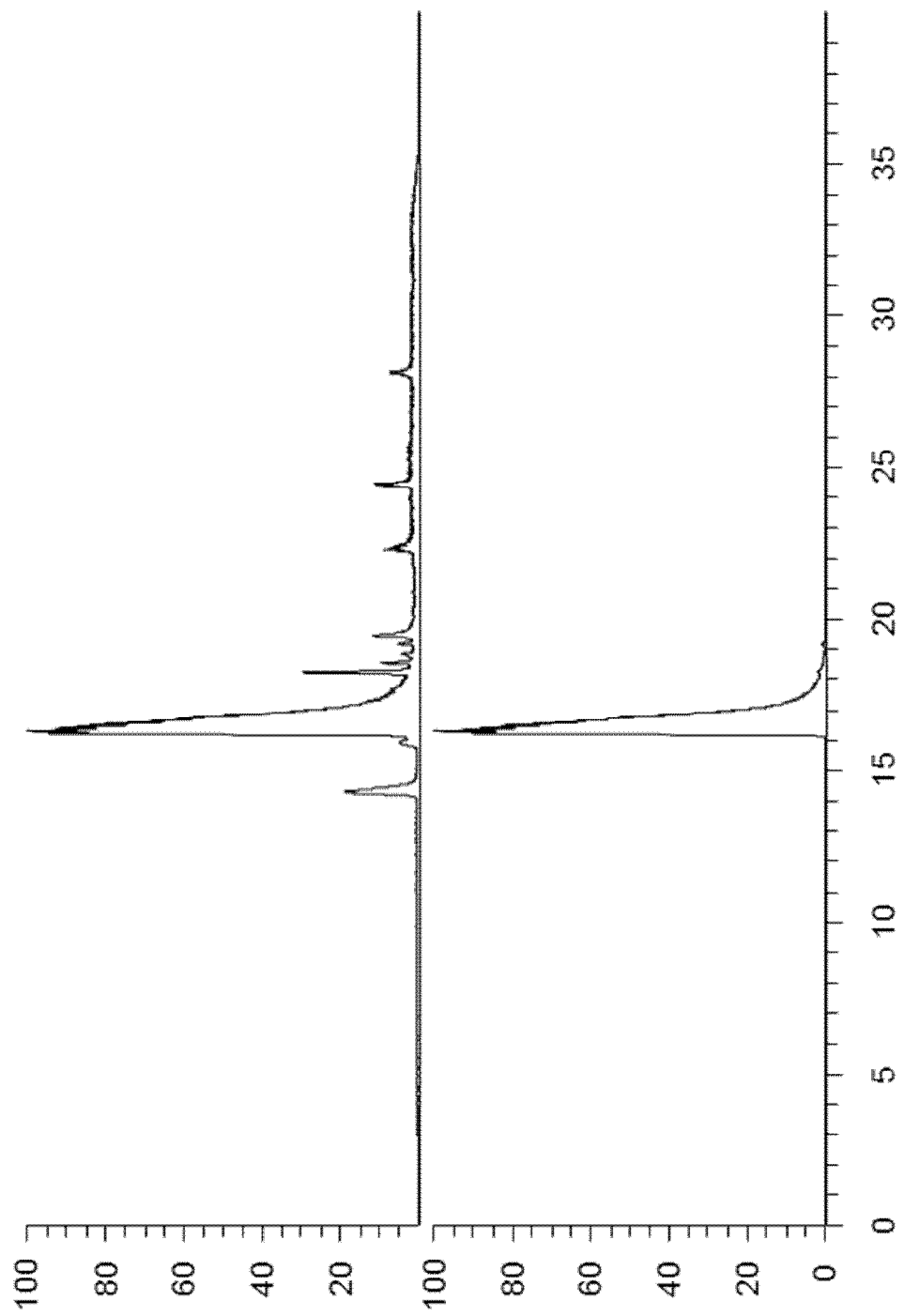

FIG. 2 displays the Total Ion Chromatogram of m/z 300 to 1500 Da (left panel when seen in portrait mode) and Extracted Ion Chromatogram of the m/z 1109.64444 (right panel when seen in portrait mode) of caspofungin hydroxylamine. A Total Ion Chromatogram is a plot of the total ion signal in each of a series of mass spectra that are recorded as a function of chromatographic retention time. An Extracted Ion Chromatogram is a plot of the signal intensity at one or more selected m/z values in a series of mass spectra that are recorded as a function of chromatographic retention time. X-axis: retention time in minutes; Y-axis: relative abundance. The elemental composition of the most abundant peak at RT 12.78 min (UV chromatogram, right panel in FIG. 1) was determined. The MS spectrum of the most abundant peak at RT 16.33 min in the Total Ion Chromatogram reveals m/z 1109.6444. The MS results are outlined in Example 3. Using the exact mass, the elemental composition of m/z 1109.64444 was determined to be $C_{52}H_{89}N_{10}O_{16}$. Based on this result, it can be concluded that the peak of interest, caspofungin hydroxylamine, has an oxygen atom more than caspofungin.

Figure 3:
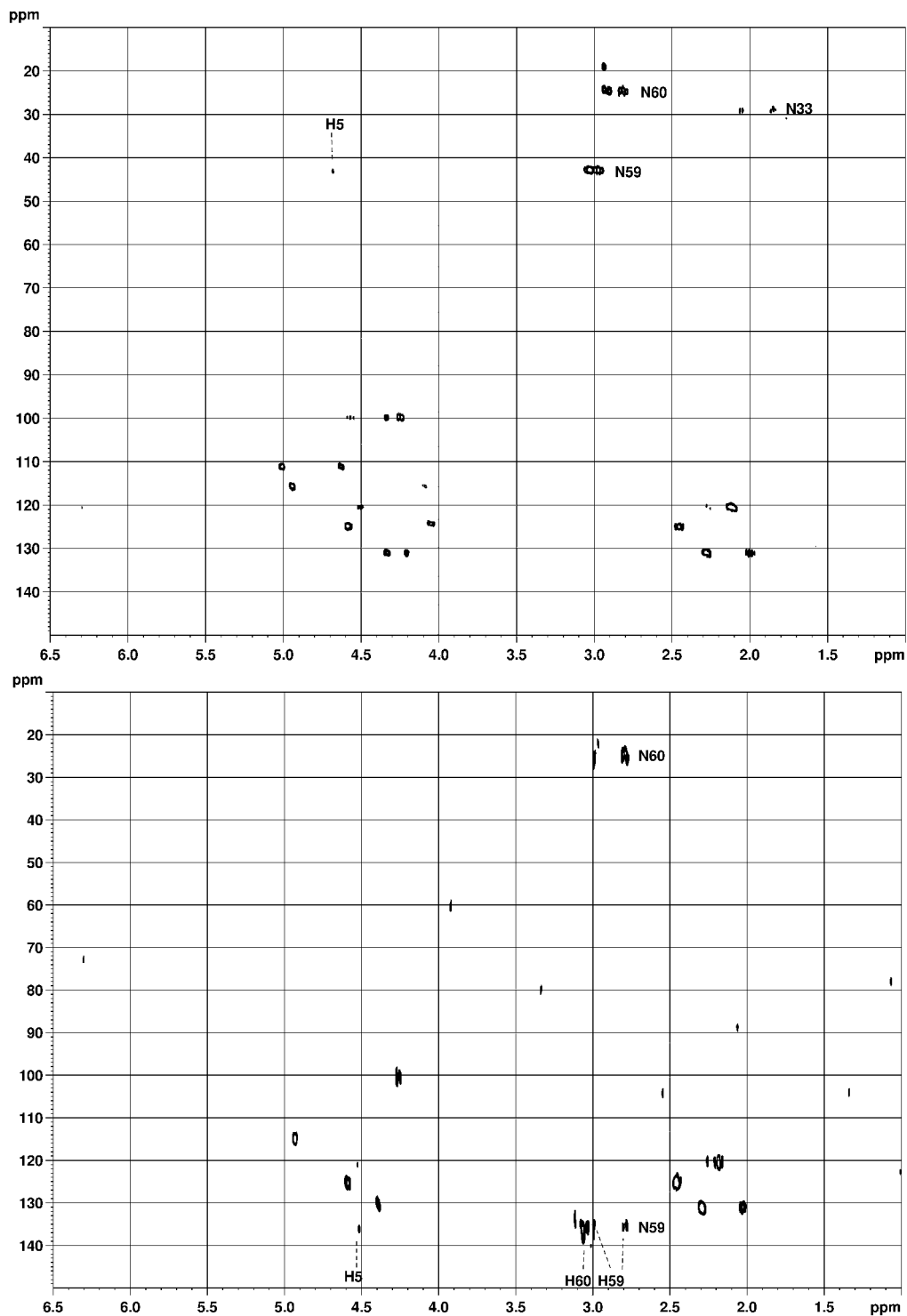

FIG. 3 displays the 15N Heteronuclear Multiple Bond Correlation (HMBC) spectra of caspofungin (top panel) and caspofungin hydroxylamine (bottom panel). The data obtained were compared with $^1H$ and $^{13}C$ NMR assignments obtained from caspofungin as in WO 2008/012310. With these assignments and the $^{15}N$-HMBC spectrum (top panel), it is straightforward to assign the nitrogen signals. The $^{15}N$ signals come in two groups, one group between 100 and 140 ppm is due to all the amide nitrogen atoms, the other group between 20 and 50 ppm is due to the amino nitrogen atoms. The HMBC spectrum shows only correlations between H and N if they are separated by two or three bonds, and such correlations may be absent in unfavourable cases. The signal at 42.9 ppm shows a correlation with both H60 protons and with H5 (atom numbering is indicated in the structural formula in the background of the description). The latter correlation demonstrates unequivocally, that the nitrogen signal at 42.9 ppm is due to N59, because N60 is separated by 5 bonds from H5. At the same time, it is observed that correlations from N59 to H59 (which would be a $^2J$ (2 bond correlation) and in principle allowed) are missing. The signal at 29 ppm shows a correlation with both H31 protons. Therefore, it must be assigned to N33. Also in this case, the $^2J$ (2 bond) correlations between N33 and H32 are missing. The signal at 24.6 ppm must be assigned to N60. Also in this case, the N60-H59 3 bond correlations are observed and not the 2 bond correlation. It should be noted, that these assignments rely on the correct assignment of H59 and H60, which was taken from WO 2008/012310.

The 15N HMBC spectrum of caspofungin hydroxylamine (bottom panel) reveals that one of the N signals in the "amine region" is missing, and an additional N is appearing at 136.0 ppm, which must be attributed to the N≥OH. This N signal has a clear correlation with H5, and therefore, this N—OH signal must be assigned to N59. Also strong correlations are observed to the protons at 3.1 ppm, which are assigned to H60 ($^3J$), and weak correlations to two other signals at 3.0 and 2.8 ppm, which are assigned to H59. The nitrogen signal at 24.2 ppm has only two strong correlations to both H59 protons, and therefore this signal is assigned to N60. Unfortunately, the signal of N33 is not visible in this spectrum due to insufficient signal/noise.

Figure 4:
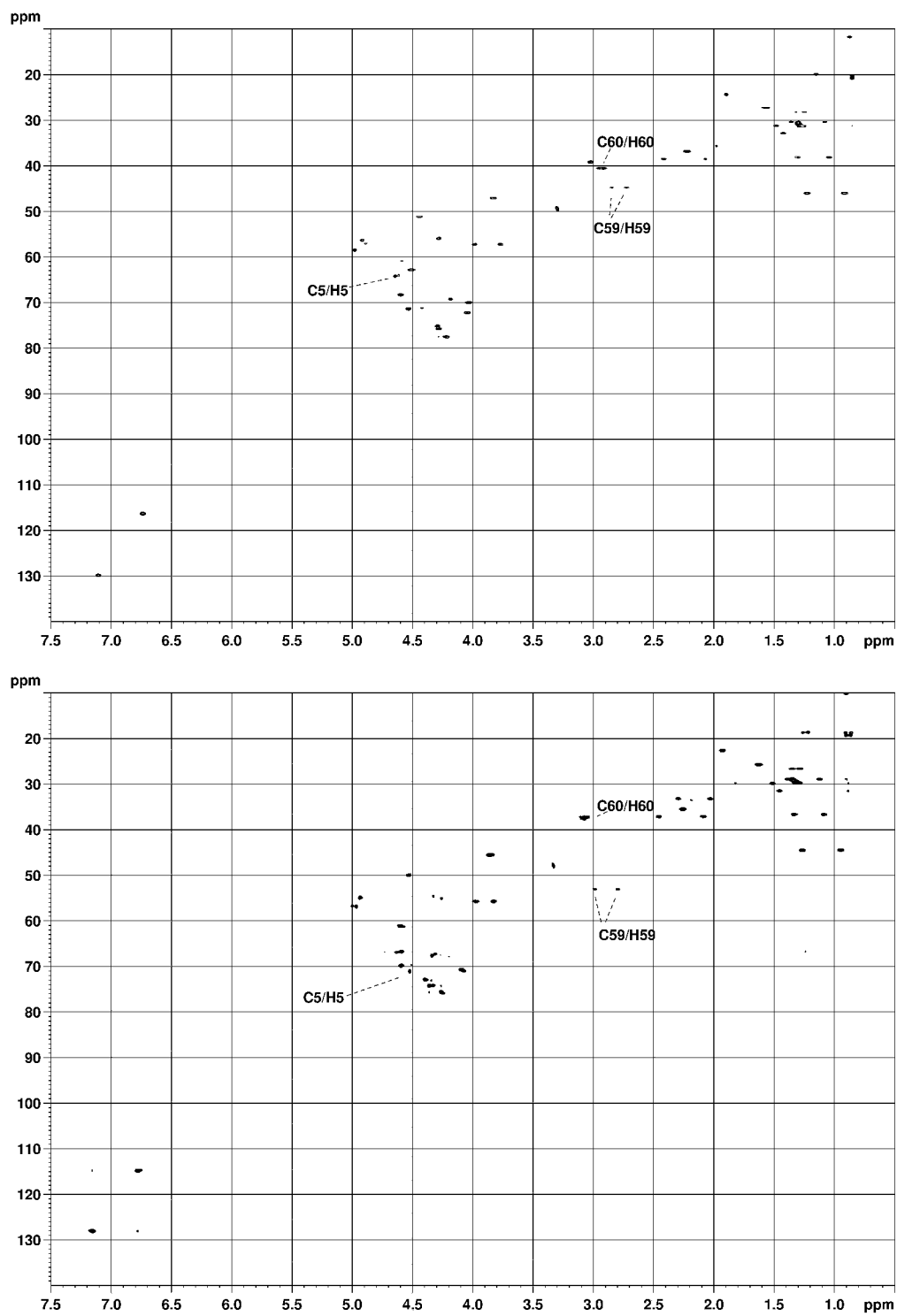

FIG. 4 displays the Heteronuclear Single Quantum Coherence (HSQC) of caspofungin (top panel) and caspofungin hydroxylamine (bottom panel). Assignments of the relevant signals of caspofungin (taken from WO 2008/012310) are given. From the HSQC spectrum of caspofungin hydroxylamine (bottom panel) it becomes clear that most signals appear at the same chemical shifts as those of caspofungin, except C59. The most important difference is the chemical shift of C59, which is now approximately 10 ppm downfield from the position in caspofungin. This is in full agreement with an oxidation of N59.

$^1H$, $^{15}N$ and $^{13}C$ NMR chemical shifts of the diaminoethane group and C5 of caspofungin are given in Table 1. $^{13}C$ Chemical shifts can be predicted by ACD chemical prediction software. These predictions are based on a large number of empirical rules and experimental data. In general $^{13}C$ chemical shifts can be predicted with higher reliability than $^1H$ chemical shifts. The predicted data are compared with the experimental data in Table 2. It is clear from Table 2 that the fit between experimental data and the predicted data for this particular structure is very good.

TABLE 1

Chemical shifts of diaminoethane group and C5 of caspofungin and caspofungin hydroxylamine

|     | Caspofungin | Caspofungin hydroxylamine |
|-----|-------------|---------------------------|
| N59 | 42.9        | 136.0                     |
| N60 | 24.6        | 24.2                      |
| C59 | 44.8        | 53.0                      |
| C60 | 40.5        | 37.5                      |
| C5  | 64.2        | 71.0                      |
| H59 | 2.84/2.72   | 2.98/2.79                 |
| H60 | 2.95/2.91   | 3.08                      |
| H5  | 4.64        | 4.52                      |

TABLE 2

Comparison between experimental $^{13}C$ shifts and shifts predicted by ACD

| | Caspofungin | | Caspofungin hydroxylamine | |
|---|---|---|---|---|
| | Experimental | Predicted | Experimental | Predicted |
| 59 | 44.8 | 48.4 | 53.0 | 53.7 |
| 60 | 40.5 | 41.3 | 37.5 | 39.0 |
| 5  | 64.2 | 67.5 | 71.0 | 71.9 |

It can be concluded that caspofungin hydroxylamine ((1) with R is hydroxyl) indeed is an oxidation product of caspofungin and that oxidation has occurred at the secondary amino group of the diaminoethane side chain.

EXAMPLES

General

Acetic acid, ethanol, ethyl acetate and methanol were obtained from Merck. A 32% solution of peracetic acid in acetic acid was obtained from Sigma-Aldrich. Caspofungin diacetate was prepared as described in WO 2010/128096.
HPLC Analysis (UV)
Column: Waters XBridge C18, length 150 mm, diameter 2.1 mm, diameter of particles 3.5 μm.
Injection volume: 5 μl
Detection: UV (210 and 270 nm)
Flow: 0.35 ml·min$^{-1}$
Column temp.: 40° C.
Mobile phase A: 700 ml 50 mM $K_2HPO_4$ (pH 7.0)+300 ml acetonitrile
Mobile phase B: 75% acetonitrile
Gradient:

| | Time (min) | | | | | |
|---|---|---|---|---|---|---|
| | 0 | 12 | 15 | 22 | 32 | 34 | 40 |
| A (%) | 100 | 84 | 84 | 0 | 0 | 100 | 100 |
| B (%) | 0 | 16 | 16 | 100 | 100 | 0 | 0 |

LC-MS Method
Column: Waters XBridge C18, length 150 mm, diameter 2.1 mm, diameter of particles 3.5 μm.
Injection volume: 5 μl
Injection mode: Full loop
Flow: 0.35 ml·min$^{-1}$
Column temp.: 40° C.
Mobile phase A: 700 ml 50 mM ammonium acetate (pH 6.8)+300 ml acetonitrile
Mobile phase B: 75% acetonitrile
Gradient:

| | Time (min) | | | | | |
|---|---|---|---|---|---|---|
| | 0 | 12 | 15 | 22 | 32 | 34 | 40 |
| A (%) | 100 | 84 | 84 | 0 | 0 | 100 | 100 |
| B (%) | 0 | 16 | 16 | 100 | 100 | 0 | 0 |

MS
LC: Accela
IMS Instrument: LTQ Orbitrap
LC/MS: ESI/pos m/z 300-1500
Resolution: 7500
NMR
The following method was used: Approximately 10 mg of the sample was weighed into a suitable vial and dissolved in approximately 0.6 ml of MeOD. The clear solution was transferred to an NMR tube and $^1H$, 2D-$^1H$-$^1H$ (COSY, TOCSY), 2D-$^1H$-$^{13}C$ (HSQC, HMBC) (700 MHz) and 2D-$^1H$-$^{15}N$ (HMBC) spectra were recorded on a 600 MHz Bruker Avance III spectrometer equipped with a cryoprobe. The measurements were performed with standard parameters at 300 K. Chemical shifts were predicted by means of ACD chemical shift prediction software version 4.07.

Example 1

Formation of caspofunqin hydroxylamine ((1), R=OH) from caspofunqin ((1), R=H) at room temperature Caspofungin diacetate (50 mg) was dissolved in ethanol (95%, 10 ml). Under stirring peracetic acid (32% in acetic acid, 20 μl) was added and the mixture was stirred at room temperature (20±3° C.) for 90 min. Samples were taken after 5, 50 and 90 min. respectively and analyzed by HPLC. Another portion of peracetic acid (32% in acetic acid, 10 μl) was added and another sample was taken after 30 min (total time after reaction start 120 min) and analyzed by HPLC. Prior to HPLC analysis all samples were diluted 10 times with methanol. HPLC results are summarized in the below Table (with the relative retention time (RRT) of caspofungin set at 1.00).

| Time | Peracetic acid | | Caspofungin | RRT 1.06 | RRT 1.36 | RRT 1.41 | RRT 1.50 |
|---|---|---|---|---|---|---|---|
| (min) | μl | Equiv. | Area % | Area % | Area % | Area % | Area % |
| 5   | 20 | 2.4 | 61.3 | 30.6 | 1.1 | 0.3 | 2.9 |
| 50  | 20 | 2.4 | 23.0 | 45.4 | 3.9 | 3.8 | 15.3 |
| 90  | 20 | 2.4 | 23.1 | 44.6 | 3.6 | 4.1 | 14.5 |
| 120 | 30 | 3.7 | 4.9  | 35.1 | 7.3 | 6.9 | 28.1 |

Example 2

Formation of caspofunqin hydroxylamine ((1), R=OH) from caspofunqin ((1), R=H) at 0-5° C.

Caspofungin diacetate (50 mg) was dissolved in ethanol (95%, 10 ml). Under stirring peracetic acid (32% in acetic acid, 30 µl) was added at 0-5° C. and the mixture was stirred at that temperature for 3 h. Samples were taken after 90 min and 3 h and analyzed by HPLC. Another portion of peracetic acid (32% in acetic acid, 10 µl) was added at 0-5° C. and another sample was taken after 60 min (total time after reaction start 4 h) and analyzed by HPLC. Prior to HPLC analysis all samples were diluted 2 times with methanol. HPLC results show that selectivity has not increased with respect to the results obtained in Example 1

Example 3

Preparation of caspofunqin hydroxylamine ((1), R=OH)

Caspofungin diacetate (1 g; 0.8 mmol) was dissolved in ethanol (95%, 20 ml). Under stirring peracetic acid (32% in acetic acid, 0.5 ml; 2.5 mmol) was added and the mixture was stirred at room temperature (20±3° C.) for 90 min. Another portion of peracetic acid (32% in acetic acid, 0.1 ml) was added bringing the molar amount of added peracetic acid to 3 mmol. After stirring for 30 minutes the mixture was concentrated under vacuum at 20° C. and the residue (5 ml) was diluted with water to 50 ml. This solution was loaded on a silica 100 $C_{18}$ column (1 Column Bed Volume (CBV): 100 ml; diameter 2.5 cm, H=20 cm), pre-equilibrated with 0.15% acetic acid. The column was eluted with 8% acetonitrile/ 0.15% acetic acid (5 CBV), 15% acetonitrile/0.15% acetic acid (10 CBV), regenerated with 75% acetonitrile (4 CBV) and equilibrated with 5 CBV 0.15% acetic acid (5 CBV). Fraction collection:
  First 1 fraction of 100 ml;
  Next fractions of about 20 ml
Fractions 23 to 40 were pooled and analyzed by HPLC: 81.5 area % of the target compound; 6.1 area % caspofungin and 8.1 area % of unknown compounds. The pooled fractions were evaporated under vacuum at 23° C. and the residue was dissolved in 0.15% acetic acid (5 ml). The resulting solution was loaded on a silica 100 $C_{18}$ column (1 Column Bed Volume (CBV): 100 ml; diameter 2.5 cm, H=20 cm), pre-equilibrated with 0.15% acetic acid. The column was eluted with 13% acetonitrile/0.15% acetic acid (10 CBV) and the following fractions were collected:
  First 1 fraction of 200 ml;
  Next fractions of about 20 ml
Fractions 37 to 40 were pooled, concentrated under vacuum at 20° C. and lyophilized to give 0.19 g of the target product as a white solid with an HPLC purity of 89.3 area %. The results of the LC/MS analysis are outlined in the below Table.

The UV and TIC chromatograms of the target product are depicted in FIGS. 1 (HPLC results of reaction mixture and purified target product) and 2 (Total Ion Chromatogram and Extracted Ion Chromatogram). For NMR data see legends to FIGS. 3 and 4.

The invention claimed is:
1. A compound of general formula (1) or a salt thereof:

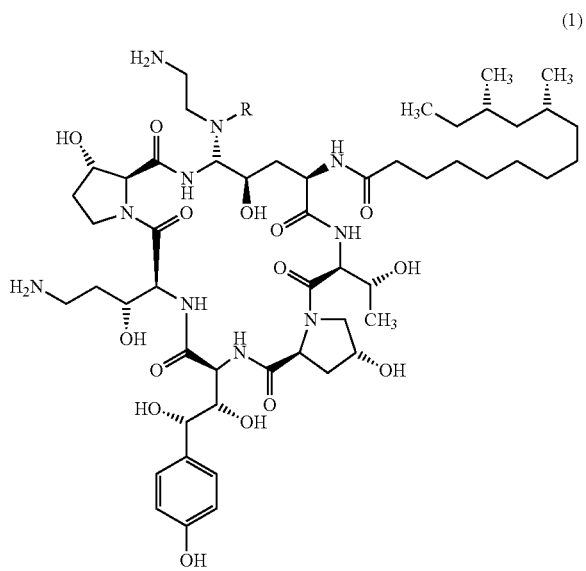

wherein R is hydroxyl.

2. The compound of claim 1, wherein the salt of the compound of formula (1) is a pharmaceutically acceptable salt.

3. The compound of claim 2, wherein the pharmaceutically acceptable salt is an acid addition salt with an organic acid comprising at least one organic acid selected from the group consisting of acetic, citric, glutamic, lactic, maleic, malic, oxalic, pamoic, propionic, succinic and tartaric acid.

4. The compound of claim 2, wherein the pharmaceutically acceptable salt is a diacetate.

5. A composition comprising caspofungin hydroxylamine or a salt thereof and a compound of general formula (1):

| m/z Da | C | H | O | N | Na | K | DBE | δ ppm | Remark | Difference vs caspofungin |
|---|---|---|---|---|---|---|---|---|---|---|
| 1109.6444 | 52 | 89 | 16 | 10 | | | 13.5 | −0.733 | [M + H]$^+$ of the peak at RT 16.33 min | + O |
| 1131.62709 | 52 | 89 | 16 | 10 | 1 | | 13.5 | −0.095 | [M + Na]$^+$ | |
| 1147.60176 | 52 | 89 | 16 | 10 | | 1 | 13.5 | 0.545 | [M + K]$^+$ | |

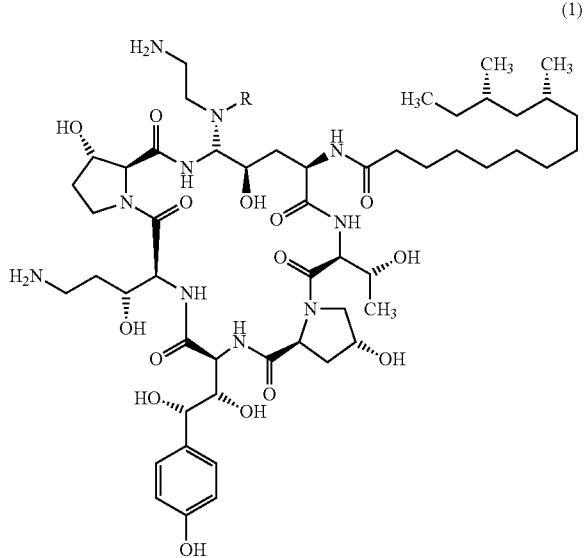

(1)

wherein R is hydrogen.

6. The composition according to claim 5, wherein the caspofungin hydroxylamine or a salt thereof is present in the composition in an amount of 0.01% to 2% based on weight.

7. A method for the preparation of a compound according to claim 1 comprising contacting caspofungin or a salt thereof with an oxidizing agent.

8. The method according to claim 7 further comprising purifying the compound by chromatography and isolating the compound.

9. The method according to claim 7, wherein the oxidizing agent is a peroxyacid.

10. The method according to claim 9, wherein the peroxyacid is at least one selected from the group consisting of m-chloroperoxybenzoic acid, peracetic acid, peroxymonosulphuric acid and peroxyphosphonic acid.

11. An antifungal medicament which comprises an antifungal effective amount of the compound according to claim 1 as an antifungal agent.

12. A method for determining quality of a caspofungin sample which comprises analyzing the caspofungin sample for trace amounts of the caspofungin hydroxylamine using the compound of claim 1 as a reference.

* * * * *